(12) United States Patent
Takahashi et al.

(10) Patent No.: US 8,354,271 B2
(45) Date of Patent: Jan. 15, 2013

(54) BIOSENSOR

(75) Inventors: Makoto Takahashi, Osaka (JP); Masaya Nakatani, Hyogo (JP); Hiroshi Ushio, Osaka (JP)

(73) Assignee: Panasonic Corporation, Osaka (JP)

( * ) Notice: Subject to any disclaimer, the term of this patent is extended or adjusted under 35 U.S.C. 154(b) by 484 days.

(21) Appl. No.: 12/668,538

(22) PCT Filed: Jul. 8, 2008

(86) PCT No.: PCT/JP2008/001814
§ 371 (c)(1),
(2), (4) Date: Jan. 11, 2010

(87) PCT Pub. No.: WO2009/008158
PCT Pub. Date: Jan. 15, 2009

(65) Prior Publication Data
US 2010/0170790 A1    Jul. 8, 2010

(30) Foreign Application Priority Data
Jul. 11, 2007  (JP) .................................. 2007-181924

(51) Int. Cl.
*G01N 27/327* (2006.01)
(52) U.S. Cl. .................................. 435/287.3; 435/287.1
(58) Field of Classification Search ................. 204/403.01–403.03; 205/777.5; 435/29, 63, 287.1, 287.3, 285.2, 288.5; 600/345, 600/900, 902; 422/98; 216/17, 41, 56, 58; 438/733, 734; 250/306, 307
See application file for complete search history.

(56) References Cited

U.S. PATENT DOCUMENTS

| | | | |
|---|---|---|---|
| 7,235,170 | B2 | 6/2007 | Watanabe et al. |
| 2003/0175841 | A1 | 9/2003 | Watanabe et al. |
| 2004/0197898 | A1 | 10/2004 | Nakatani et al. |
| 2005/0072670 | A1 | 4/2005 | Hasegawa |
| 2005/0214740 | A1 | 9/2005 | Ushio et al. |
| 2005/0221469 | A1 | 10/2005 | Nakatani et al. |
| 2009/0178922 | A1* | 7/2009 | Nakatani et al. ......... 204/403.01 |

FOREIGN PATENT DOCUMENTS

| | | |
|---|---|---|
| JP | 2001-343385 | 12/2001 |
| JP | 2003-065997 A | 3/2003 |
| JP | 2004-069309 A | 3/2004 |
| JP | 2004-271331 A | 9/2004 |
| JP | 2004-350649 A | 12/2004 |

(Continued)

OTHER PUBLICATIONS

International Search Report for PCT/JP2008/001814, Oct. 21, 2008.

(Continued)

*Primary Examiner* — J. Christopher Ball
(74) *Attorney, Agent, or Firm* — RatnerPrestia

(57) ABSTRACT

A sensor includes a diaphragm having a through-hole (1), and includes a frame supporting a diaphragm and having a cavity. Kerfs are formed in a frame so as to extend from an end surface of the frame, and the wall surfaces of the kerfs are made hydrophilic. This structure can suppress the occurrence of bubbles in the vicinity of the through-hole, and efficiently remove the remaining bubbles. As a result, the bubbles adhering to the vicinity of the through-hole can be removed, and the measuring reliability of the sensor can be improved.

8 Claims, 4 Drawing Sheets

FOREIGN PATENT DOCUMENTS

| | | |
|---|---|---|
| JP | 2005-265758 A | 9/2005 |
| WO | WO 99/66329 | 12/1999 |
| WO | WO 02/55653 A1 | 1/2002 |
| WO | WO 02/093151 A1 | 11/2002 |
| WO | WO 2007/072790 A1 | 6/2007 |
| WO | WO 2008/004476 A1 | 1/2008 |

OTHER PUBLICATIONS

T. Sordel et al. A Silicon-Based Multi-Patch Device: Application for Ionic Currents Sensing on Single Cells, 8$^{th}$ International Conference on Miniaturized Systems for Chemistry and Life Sciences, Sep. 26-30, 2004, pp. 521-522, France.

* cited by examiner

BIOSENSOR

THIS APPLICATION IS A U.S. NATIONAL PHASE APPLICATION OF PCT INTERNATIONAL APPLICATION NO. PCT/JP2008/001814.

TECHNICAL FIELD

The present invention relates to a biosensor, such as a cell electrophysiological sensor, used to measure the extracellular potential of a cell or physicochemical changes occurring in cellular activity.

BACKGROUND ART

A patch clamp method is known as a conventional method for clarifying the function of ion channels present in a cell membrane, using the electrical activity of the cell as an index, or screening (testing) a medicine.

However, the patch clamp method requires special technologies and techniques in preparation and operation of a micropipette for sucking a micropart (referred to as a patch) of a cell membrane. Therefore, the method takes much time to measure one specimen, and thus is not suitable for applications of screening a large amount of candidate chemical compounds at high speed.

On the other hand, in recent years, a flat panel-shaped microelectrode probe made by a micromachining technology has been developed. A method using such a flat panel-shaped microelectrode probe is suitable for the automation system that does not require insertion of micropipettes into individual cells.

As this type of technology, Patent Literature 1, for example, discloses the following technology: a plurality of through-holes are formed through a cell-holding membrane, specimen cells are attached to the openings of the through-holes, and the voltage-dependent ion channel activity of the specimen cells is measured with a measuring electrode disposed below the through-holes.

Non Patent Literature 1 discloses the following technology: a hole of 2.5 μm is formed through silicon oxide cell-holding membrane, an HEK293 cell, a type of cultured human cell line, is held in this hole with high adherence ensured therebetween, and the extracellular potential is measured with high accuracy.

Further, Patent Literature 2 discloses a cell electrophysiological sensor where a cell is trapped (captured) in a recess formed in a cell-holding membrane, and the potential difference between a reference electrode and a measuring electrode disposed on both sides of the cell-holding membrane is obtained to analyze the functionality of the ion channels in the cell, for example.

In this manner, in order to screen a large amount of candidate chemical compounds at high speed, the potential difference between the reference electrode and the measuring electrode is obtained with a cell trapped in a through-hole or the recess.

As such a conventional cell electrophysiological sensor, the electrophysiological sensor disclosed in Patent Literature 2 is detailed with reference to FIG. 7. As shown in FIG. 7, conventional cell electrophysiological sensor 31 has cell-holding membrane 32, recess 33 formed in the top surface of cell-holding membrane 32, and through-hole 34 connecting the bottom portion of recess 33 and the bottom surface of cell-holding membrane 32. Further, the sensor has reference electrode 35 disposed above cell-holding membrane 32 and measuring electrode 36 disposed inside of through-hole 34.

Measuring electrode 36 is coupled to a signal detector via wiring 37. Cell-holding membrane 32 is disposed inside of well 38.

Next, a measuring method using cell electrophysiological sensor 31 is described. First, a cell and electrolytic solution 40 are placed in well 38. The cell is trapped and held by recess 33. The cell held by recess 33 is referred to as specimen cell 39 hereinafter.

During measurement, specimen cell 39 is sucked with a suction pump, for example, from the downward direction of through-hole 34, and held onto the opening of through-hole 34 in intimate contact therewith. That is, through-hole 34 has a function similar to that of the tip hole of a glass pipette. The functionality and pharmacodynamic reaction of the ion channels in specimen cell 39 are analyzed by measuring the voltage or current between reference electrode 35 and measuring electrode 36 before and after the reaction and obtaining the potential difference between the inside and outside of the cell.

However, conventional cell electrophysiological sensor 31 has errors in the measurements of the potential difference between reference electrode 35 and measuring electrode 36, so that the measuring reliability of cell electrophysiological sensor 31 is degraded.

This is caused by the following reason. Bubbles are likely to remain in a portion of the inner wall surface of well 38 having low hydrophilic properties, or a portion having asperities on the periphery of through-hole 34. The resistance of these bubbles is so large that the presence of the bubbles causes variations in measurements.

In particular, bubbles occurring in the vicinity of through-hole 34 are the factors for causing great variations in the measurements of the current or voltage detected in measuring electrode 36.

[Patent Literature 1] Japanese Translation of PCT Publication No. 2002-518678
[Patent Literature 2] International Publication No. 02/055653 Pamphlet
[Non Patent Literature 1] T. Sordel et al, Micro Total Analysis Systems 2004, p 521-522 (2004)

SUMMARY OF THE INVENTION

The present invention is directed to provide a biosensor that has high measuring reliability provided by suppressing the occurrence of bubbles in the vicinity of a specimen holder, and efficiently removing the bubbles.

The present invention includes a diaphragm having a through-hole, and includes a frame supporting the diaphragm and having a cavity. Kerfs are formed in the frame so as to extend from the end surface of the frame, and the wall surfaces of the kerfs are made hydrophilic.

This structure can suppress the occurrence of bubbles in the vicinity of the specimen holder, and efficiently remove the remaining bubbles. As a result, the bubbles adhering to the vicinity of the through-hole can be removed, and the measuring reliability of the sensor can be improved.

REFERENCE MARKS IN THE DRAWINGS

Figure 1:
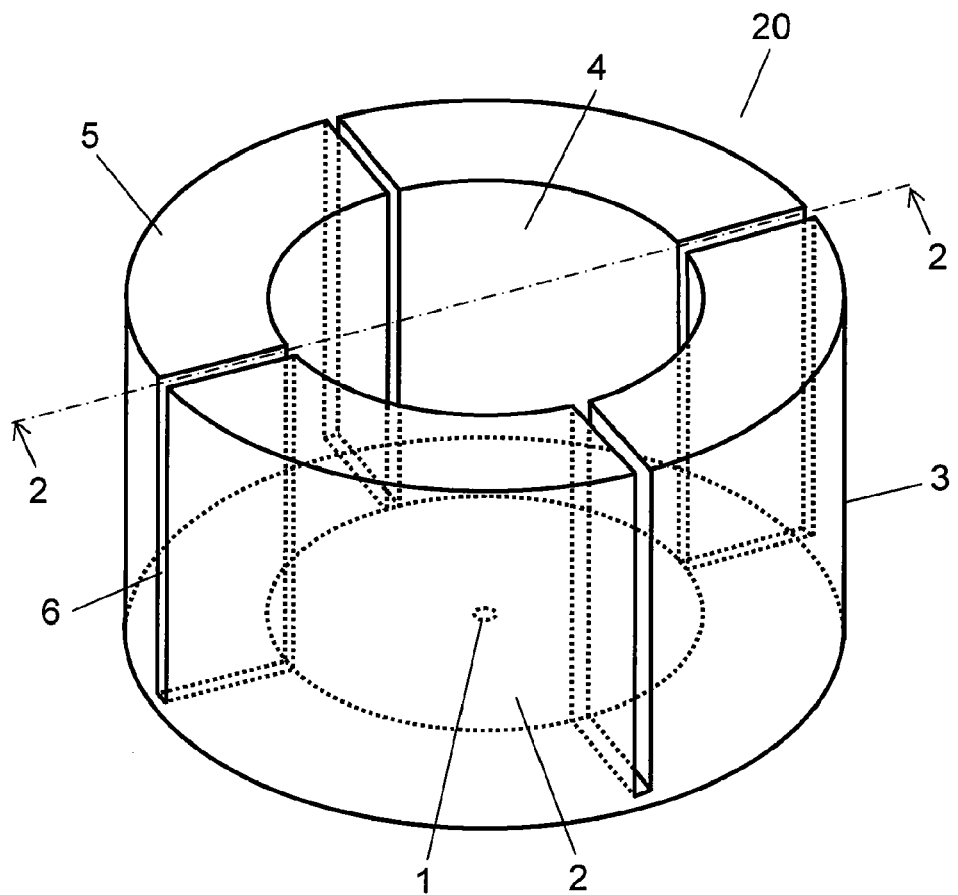
FIG. 1 is a sectional perspective view of a cell electrophysiological sensor in accordance with a first exemplary embodiment of the present invention.

1 Through-hole
2 Diaphragm
3 Frame
3a Inner circumferential part
4 Cavity
5 End surface
6 Kerf
6a Wall surface
9 Cell
9a Specimen cell
10 Extracellular fluid
11 Intercellular fluid
12 Reference electrode
13 Measuring electrode
14 Baffle plate
14a First plate
14b Second plate
15 Well
16 Fluid channel
17 Case
19 Opening
20 Cell electrophysiological sensor

DETAILED DESCRIPTION OF PREFERRED EMBODIMENTS

Figure 2:
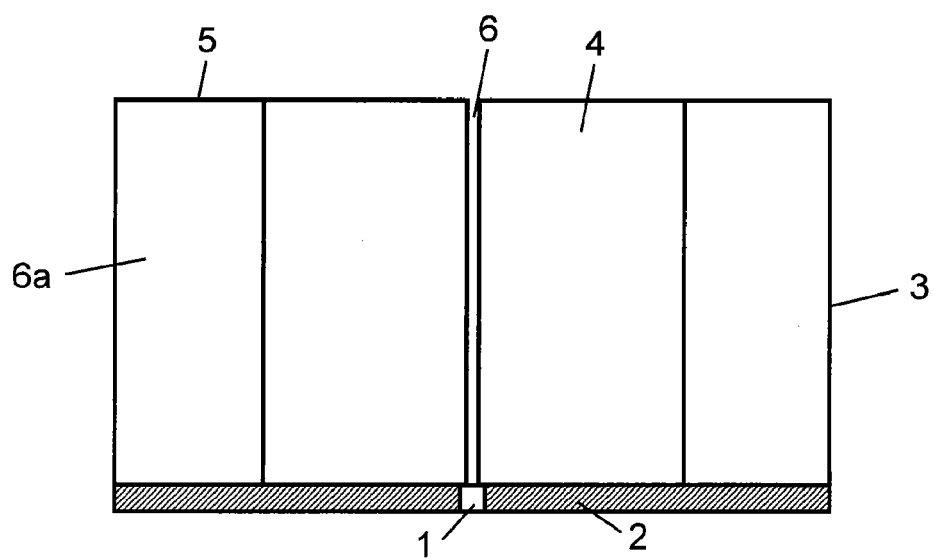
FIG. 2 is a sectional view taken on line 2-2 of FIG. 1.
Figure 3:
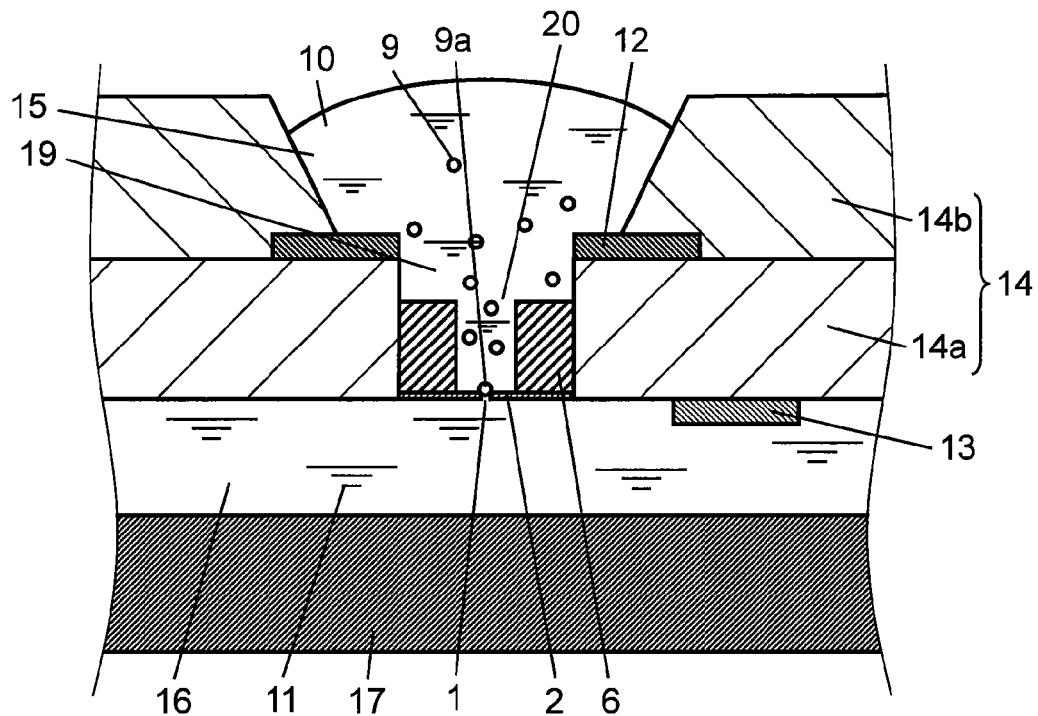
FIG. 3 is a sectional view showing a cell potential measuring device that includes the cell electrophysiological sensor in accordance with the first exemplary embodiment.

Hereinafter, a biosensor of the present invention is described, using a cell electrophysiological sensor as an example, with reference to the accompanying drawings.
First Exemplary Embodiment FIG. 1 is a sectional perspective view of a cell electrophysiological sensor in accordance with the first exemplary embodiment of the present invention. FIG. 2 is a sectional view taken on line 2-2 of FIG. 1. FIG. 3 is a sectional view showing a cell potential measuring device for explaining a method for measuring an electrophysiological phenomenon of cells.

With reference to FIG. 1 and FIG. 2, cell electrophysiological sensor 20 of this exemplary embodiment has thin plate-shaped diaphragm 2 having at least one through-hole 1, and frame 3 for fixedly supporting diaphragm 2 and facilitating fixation of the sensor to a measuring device, for example. Through-hole 1 captures and holds a cell, and serves as a specimen holder.

At least one through-hole 1 is sufficient. In order to measure a plurality of cells 9 (see FIG. 3) at the same time, a plurality of through-holes 1 can be formed. With this structure, the plurality of cells 9 can be measured at the same time to improve the S/N ratio.

Cavity 4 capable of pooling a liquid that contains cells, for example, is formed in frame 3. In frame 3, kerfs 6 are formed so as to extend from end surface 5. The wall surfaces 6a of kerfs 6 are surface-treated so as to have hydrophilic properties.

Kerfs 6 are formed in frame 3 and at least wall surfaces 6a of kerfs 6 are made hydrophilic. This structure suppresses the occurrence of bubbles and efficiently removes the bubbles when a liquid in the form of a droplet is injected into cavity 4 using a dispenser, for example, as will be described later.

In this exemplary embodiment, wafers of silicon, for example, having high obtainability and processability, are prepared. Then, by a general etching process using a photolithography technique, for example, a plurality of cell electrophysiological sensors 20 are collectively produced. With this method, cell electrophysiological sensors having high dimensional accuracy and microshapes can be produced efficiently.

Further, as described in this exemplary embodiment, it is preferable in terms of mechanical strength and handling that frame 3 supporting diaphragm 2 and having cavity 4 for pooling a liquid is formed unitary with diaphragm 2 from silicon, for example.

In order to provide hydrophilic properties to the surfaces of wall surfaces 6a, it is preferable that carbon molecules adhering to the surfaces are removed so that the surfaces are made clean. Immediately thereafter, the frame is stored in a container filled with pure water. Thereby, the cleanliness of the surfaces can be maintained. Preferably, the hydrophilic properties at this time are such that the contact angle is equal to or smaller than 10°. This contact angle can be measured by applying a droplet of de-ionized pure water to the surface of the object to be measured.

Further, as another means for enhancing hydrophilic properties, coating the surfaces of wall surfaces 6a with an insulating film of silicon dioxide, for example, is effective.

A description is provided for a structure of a cell potential measuring device for measuring electrophysiological activity of cells that includes cell electrophysiological sensor 20 of this exemplary embodiment structured as above.

FIG. 3 is a sectional view of an essential part showing a cell potential measuring device that includes cell electrophysiological sensor 20 in accordance with this exemplary embodiment.

With reference to FIG. 3, baffle plate 14 formed of a laminate of first plate 14a, i.e. a lower layer, and second plate 14b, i.e. an upper layer, is fixed to the outer edges of case 17 in the shape of a rectangular parallelepiped plate having an opening in the top surface. First plate 14a has a plurality of openings 19 formed in matrix. Inside of each opening 19, cell electrophysiological sensor 20 as described above is set. In second plate 14b, well 15 for pooling a liquid is formed so as to correspond to each opening 19. Extracellular fluid 10 is supplied to well 15, and intercellular fluid 11 is supplied to case 17. Thus baffle plate 14 serves to separate extracellular fluid 10 and intercellular fluid 11.

In terms of productivity, processability, and dimensional accuracy, it is preferable that case 17 and baffle plate 14 (first plate 14a and second plate 14b) are formed of resin made of insulator, such as plastics.

Cell electrophysiological sensor 20 is joined to the inside of opening 19 without gaps so that diaphragm 2 is on the bottom side and no fluid leaks into opening 19. Thus case 17 is partitioned into two vertical areas by diaphragm 2 and first plate 14a. The two vertical areas partitioned by diaphragm 2 and first plate 14a separately pool a liquid, e.g. extracellular fluid 10 and culture solution, and a liquid, e.g. intercellular fluid 11 and medical solution. Extracellular fluid 10 includes a liquid that contains cells 9 or the like. Among a plurality of cells 9 suspended in such a liquid, cell 9 is sucked with a suction mechanism, such as a suction pump, from the downward direction of baffle plate 14, and held so as to block through-hole 1. Such a cell is specimen cell 9a. With this operation, the liquid above these specimen cells 9a and the liquid below the cells move only via through-holes 1. In this exemplary embodiment, the appropriate suction force of the suction mechanism ranges from 2 kPa to 10 kPa. The suction force varies with the lengths of through-hole 1.

The undersurface of first plate 14a and the bottom of case 17 form fluid channel 16. A liquid, e.g. intercellular fluid 11 and medical solution, can be charged into or removed from fluid channel 16 with a fluid delivery mechanism, such as a micropump.

Further, on the top side of baffle plate 14, reference electrode 12 made of chromium, titanium, copper, gold, platinum, silver, or silver chloride is disposed in extracellular fluid 10. On the bottom side of baffle plate 14, measuring electrode 13 similarly made of chromium, titanium, copper, gold, platinum, silver, or silver chloride is disposed in intercellular fluid 11.

These reference electrode 12 and measuring electrode 13 may be interchanged. As reference electrode 12 and measuring electrode 13, a needle-shaped microelectrode probe may be used.

Next, a description is provided for a method for measuring cell potential, using the cell potential measuring device structured as above.

First, a predetermined amount of extracellular fluid 10, i.e. a liquid containing cells 9 dispersed therein, is injected into cavity 4, using an automatic dispenser, for example. Generally, in this case, the liquid has a spherical appearance and shape formed by surface tension. The liquid is dispensed into cavity 4 in that shape.

At this time, in order to measure electrochemical changes in specimen cell 9a stably with high accuracy, it is important to charge the liquid without bubbles remaining in the vicinity of through-hole 1.

When end surface 5 of frame 3 of cell electrophysiological sensor 20 is formed of one plane without kerfs 6, for example, a droplet at the tip of a micropipette dispensed from the dispenser can completely block the entrance of cavity 4 in some cases. This makes the inside of cavity 4 hermetically sealed. Thus the gas, such as air, present inside of cavity 4 has no escape route and remains as bubbles during measurement. Further, the lack of the escape route hinders smooth injection of the droplet into cavity 4.

In contrast, in this exemplary embodiment, kerfs 6 are formed in frame 3 so as to extend from end surface 5. Thus the gas, such as air, present inside of cavity 4 can escape in the upward direction and be released outside easily. Therefore, no gas remains inside of cavity 4 as air bubbles.

At the same time, when a droplet formed of extracellular fluid 10 makes contact with end surface 5 of frame 3, kerfs 6 have hydrophilic wall surfaces 6a. Thus wall surfaces 6a of kerfs 6 have improved wettability to the liquid, and the liquid can be charged into cavity 4 promptly. That is, while wetting wall surfaces 6a of kerfs 6 by means of the surface tension of extracellular fluid 10 forming the droplet, the liquid made of extracellular fluid 10 can be charged into cavity 4 together with cells 9. Thus the liquid made of extracellular fluid 10 can be charged without bubbles in the vicinity of through-hole 1.

Further, in this exemplary embodiment, as shown in FIG. 2, each kerf 6 is formed so that the bottom surface of kerf 6 is flush with the surface of diaphragm 2. This allows prompt permeation of the liquid to diaphragm 2 and prompt removal of air bubbles remaining on the surface of diaphragm 2.

When such kerf 6 has a width of 10 to 150 µm, the liquid efficiently permeates, by means of surface tension, and the advantage of kerf 6 can be maximized. More preferably, kerf 6 has a width of 25 to 100 µm. That is, a kerf having a width smaller than 25 µm is too narrow to allow the entry of the droplet into the kerf by means of the surface tension of the liquid in some cases. A kerf having a width larger than 100 µm is so wide that a large bubble can remain in the kerf in some cases.

Further, as shown in FIG. 1, forming a plurality of kerfs 6 in a radial configuration can ensure contact of a part of the droplet with a part of kerfs 6 even when the tip of the dispenser tilts or the droplet has a less symmetrical shape. This structure can reliably suppress the occurrence of bubbles from wall surfaces 6a of kerfs 6 formed in frame 3, and allows a liquid, such as extracellular fluid 10, to be charged while remaining bubbles are considerably reduced.

In this manner, in this exemplary embodiment, a liquid can be charged into cell electrophysiological sensor 20 without remaining bubbles as shown in FIG. 3.

Thereafter, using a suction mechanism, such as a suction pump, a predetermined pressure difference is caused between the top and bottom sides of baffle plate 14 so that the bottom side of baffle plate 14 has a lower pressure. At this time, one cell 9 is attracted to the opening of through-hole 1 and trapped onto through-hole 1. Cell 9 trapped onto through-hole 1 is specimen cell 9a. When this pressure difference is maintained, sufficient adherence is ensured, and thus an electrical resistance is provided between extracellular fluid 10 and intercellular fluid 11 in fluid channel 16. That is, a large resistance is indicated between reference electrode 12 disposed in well 15 and measuring electrode 13 disposed in fluid channel 16.

Specifically, when one side of fluid channel 16 is sealed and the fluid channel is depressurized from the other side, cell 9 is attracted to through-hole 1. At last, specimen cell 9a blocks through-hole 1, and is trapped therein. With this operation, the resistance between cavity 4 filled with extracellular fluid 10 and fluid channel 16 filled with intercellular fluid 11 sufficiently increases to 1 GΩ, for example.

Incidentally, in a state where well 15 is filled with extracellular fluid 10, i.e. in a state where specimen cell 9a is not trapped with a suction mechanism, a resistance in the order of 100 kΩ to 10 MΩ can be observed between reference electrode 12 and measuring electrode 13. This is because the electrolytic solution permeates into through-hole 1 disposed in cell electrophysiological sensor 20 and an electrical circuit is formed between reference electrode 12 and measuring electrode 13. By measuring the resistance in such a state, it is determined that through-hole 1 is normally opened. When through-hole 1 is not opened, no electrical circuit is formed between reference electrode 12 and measuring electrode 13, so that the resistance takes a sufficiently large value in the order of 1 GΩ.

The liquid to be charged into well 15 is not specifically limited. Besides extracellular fluid 10, a culture solution for culturing cells 9, or other chemical solutions may be used.

Next, the suction force of the suction mechanism is controlled so that depressurization is continued until a part of the membrane of specimen cell 9a is broken. Further, from the bottom side of through-hole 1, intercellular fluid 11 is introduced into specimen cell 9a. This operation can bring a part of specimen cell 9a into contact with intercellular fluid 11, and specimen cell 9a into a state where its electrochemical changes can be measured.

Alternatively, while specimen cell 9a is securely trapped in through-hole 1, a medical solution working to dissolve the outer wall of specimen cell 9a, such as nystatin, is introduced into fluid channel 16. With this operation, a microhole is formed in specimen cell 9a, so that a part of specimen cell 9a can be brought into contact with intercellular fluid 11. Therefore, also in this case, as similar to the above, specimen cell 9a is brought into a state where its electrochemical changes can be measured.

Here, for mammal muscle cells, for example, extracellular fluid 10 is an electrolytic solution that typically contains approximately 4 mM of $K^+$ ions, approximately 145 mM of $Na^+$ ions, and approximately 123 mM of $Cl^-$ ions. For mammal muscle cells, for example, intercellular fluid 11 is an electrolytic solution that typically contains approximately 155 mM of $K^+$ ions, approximately 12 mM of $Na^+$ ions, and approximately 4.2 mM of $Cl^-$ ions.

Next, changes in current or voltage are measured between reference electrode 12 and measuring electrode 13. Thereby, electrochemical changes in specimen cell 9a are measured and detected. For stable measurement and detection, a state where specimen cell 9a is securely trapped in through-hole 1 needs to be kept stable. For this purpose, preferably, through-hole 1 has a shape slightly smaller than that of specimen cell 9a so that specimen cell 9a can be fixed onto through-hole 1 so as to block the through-hole, with a suction mechanism, for example. For this purpose, in this exemplary embodiment, the diameter of through-hole 1 is set to 3 μm.

As described above, when the size of cell 9 ranges from approximately 5 to 50 μm, in order to keep high adherence between cell 9 and through-hole 1, it is preferable to set the diameter of through-hole 1 to 3 μm or smaller. However, the optimum size of through-hole 1 can be determined according to the shape and nature of cells 9 to be measured.

When a stimulation of a compound, such as a medicine, is given to specimen cell 9a, specimen cell 9a shows an electrophysiological response. As a result, between reference electrode 12 and measuring electrode 13, an electrochemical change can be observed as an electrical response in voltage, current, or the like.

The above chemical stimulations are caused by chemicals, poisons, or the like. Besides these stimulations, physical stimulations are caused by mechanical modification, light, heat, electricity, electromagnetic waves, or the like.

When specimen cell 9a actively reacts to these stimulations, specimen cell 9a releases or absorbs various ions through ion channels present in its cell membrane. Then, ion current through specimen cell 9a is generated, and changes the gradient of potential inside and outside of this specimen cell 9a. That is, this change can be detected by measuring the voltage or current between reference electrode 12 and measuring electrode 13 before and after the reaction.

In this exemplary embodiment, a description has been provided for an example of cell electrophysiological sensor 20 in the cell potential measuring device where diaphragm 2 is disposed on the bottom side for measurement. However, diaphragm 2 can be disposed on the top side for measurement. In this case, the occurrence and remaining of bubbles in intercellular fluid 11 can be suppressed, and specimen cell 9a makes intimate contact with the opening of through-hole 1 on the side opposite to the side in the above description. Such a structure can be used for a case where the intimate contact of specimen cell 9a with a hole formed through a flat surface is convenient. Preferably, which structure to use is determined according to the nature of specimen cell 9a, for each case.

When an electrical response is measured between reference electrode 12 and measuring electrode 13, any bubble present in the vicinity of through-hole 1 increases the resistance, thus causing variations in the measurements of the current and voltage detected in measuring electrode 13. However, cell electrophysiological sensor 20 of this exemplary embodiment structured as shown in FIG. 1 can suppress the occurrence of bubbles and remove the remaining bubbles promptly as described above. Thus a cell electrophysiological sensor capable of measuring microchanges in current or voltage with high accuracy and improved measuring reliability can be provided.

Preferably, besides wall surfaces 6a as described in this embodiment, all the surfaces to be in contact with the liquid, such as the inner wall surface of cavity 4, and inner wall surfaces of diaphragm 2 and through-hole 1 are made hydrophilic. This structure can enhance wettability to the liquid for various measurements, and suppress the occurrence of bubbles.

Further, when a plurality of kerfs 6 are formed so as to have widths of different dimensions and shapes, kerf 6 facilitating escape of bubbles and kerf 6 facilitating permeation of the liquid can be mixed. Because the etching speed in processing of each kerf 6 depends on the dimension of the width of the kerf, kerfs 6 can be formed so as to have bottom shapes where bottom surfaces are at different heights.

Extracellular fluid 10 and intercellular fluid 11 may have different compositions as described in this embodiment, or the same composition.

It is preferable in terms of processability, mechanical strength, or the like, that the thickness of diaphragm 2 ranges from 10 to 300 μm. Diaphragm 2 having a thickness smaller than 10 μm has cracks easily when sucked with a suction part, for example, from the bottom side of through-hole 1. A diaphragm having a thickness larger than 300 μm cannot be processed easily by etching, for example, and requires more processing time.

In this embodiment, diaphragm 2 has a disk shape. However, diaphragms in other shapes, such as a quadrangular shape, can provide the similar advantage.

It is preferable in terms of productivity that the inner diameter of cavity 4 ranges from 100 μm to 1.0 mm. Cavity 4 having an inner diameter smaller than 100 μm is so small that a liquid cannot be dispensed easily therein, and many bubbles remain. When the inner diameter exceeds 1.0 mm, the productivity of the sensor is decreased. Further, when a liquid containing a small amount of cells 9 is measured, diaphragm 2 is too large for cells 9 to move thereon. This lowers the probability that cell 9 is captured in through-hole 1, and is not preferable.

Second Exemplary Embodiment

Figure 4:
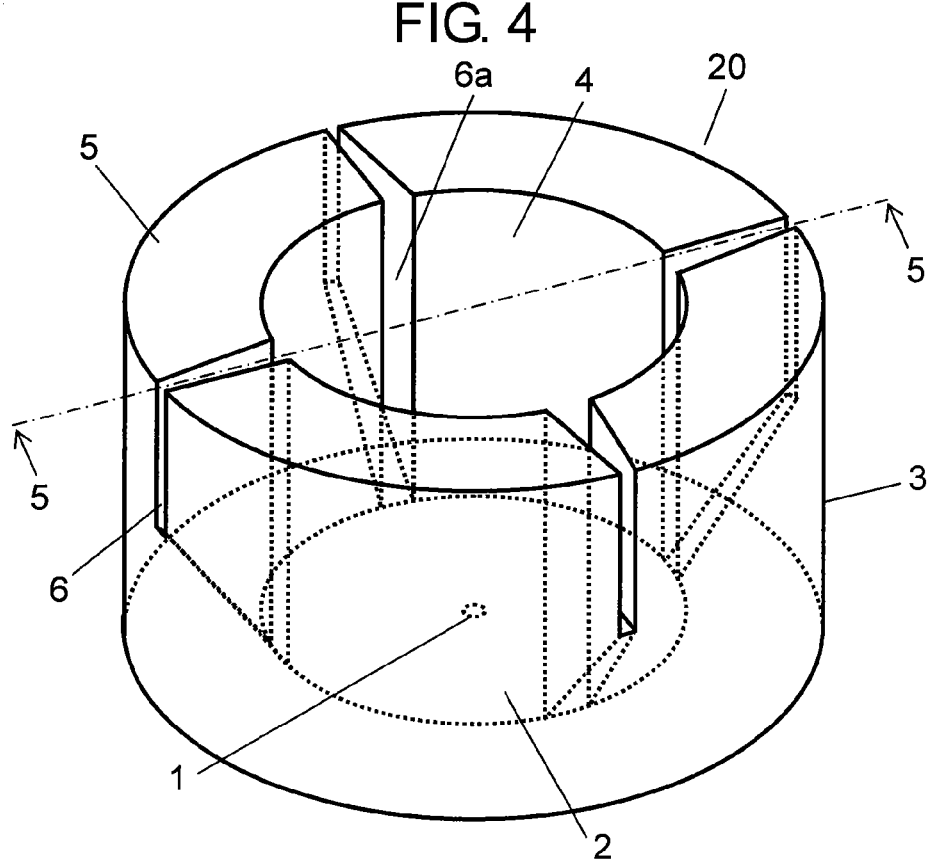
FIG. 4 is a sectional perspective view of a cell electrophysiological sensor in accordance with a second exemplary embodiment of the present invention.
Figure 5:
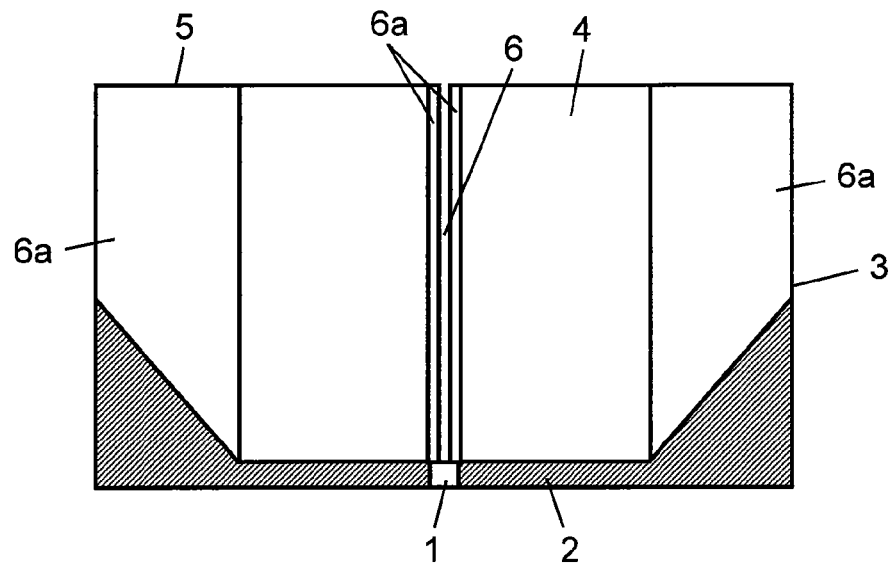
FIG. 5 is a sectional view taken on line 5-5 of FIG. 4.

A description is provided for a cell electrophysiological sensor in accordance with the second exemplary embodiment of the present invention with reference to FIG. 4 and FIG. 5.

FIG. 4 is a sectional perspective view of the cell electrophysiological sensor in accordance with the second exemplary embodiment. FIG. 5 is a sectional view taken on line 5-5 of FIG. 4.

The structure of the cell electrophysiological sensor of this exemplary embodiment largely differs from that of the cell electrophysiological sensor of the first exemplary embodiment in the following point: in the opening shape of kerf 6 on end surface 5, the width of the kerf increases from the outer circumference to the inner circumference of frame 3.

This structure enhances the affinity of a liquid that flows from well 15 or baffle plate 14 by means of the surface tension, and allows bubbles to escape from the inner circumferential part of kerf 6 more effectively.

Further, the structure of the cell electrophysiological sensor of this exemplary embodiment largely differs from that of the cell electrophysiological sensor of the first exemplary embodiment in the following point: in the shape of kerf 6 in the depth direction, kerf 6 has an inclined bottom shape so that the depth of kerf 6 is increased from the outer circumference to diaphragm 2.

In addition to suppression of the occurrence of bubbles and efficient removal of the bubbles, this structure allows cells 9 to fall along the bottom shape of kerf 6 to the vicinity of through-hole 1. Thus, even in a small amount of cells 9, specimen cell 9a can be fixed onto through-hole 1 promptly. That is, a droplet containing cells 9 and dispersed at a high position of end surface 5 from a dispenser makes contact with a part of the nearest kerf 6, and moves on hydrophilic wall surfaces 6a forming this kerf 6 by means of the surface tension of the liquid. Thereafter, in the vicinity of frame 3, the liquid can be guided to the center of diaphragm 2 where through-hole 1 is present. Thus the occurrence of bubbles can be suppressed and remaining bubbles can be removed efficiently.

Kerf 6 having an inclined bottom surface as described above can be formed by changing the width of kerf 6. That is, as shown in FIG. 4, the width of kerf 6 is increased from the outer circumferential part to the inner circumferential part of frame 3, so that the kerf has a wider opening shape in the inner circumferential part. When a silicon wafer having such an opening shape is etched, the etching speed on the inner circumferential side is higher and the etching speed on the outer circumferential side is lower. Using the difference in the etching speed, kerf 6 can be processed to have an inclined bottom surface.

In this exemplary embodiment, both of opening shape of kerf 6 on end surface 5 and bottom shape of kerf 6 are changed. However, the change of either one does not impede the present invention.

Third Exemplary Embodiment

Figure 6:
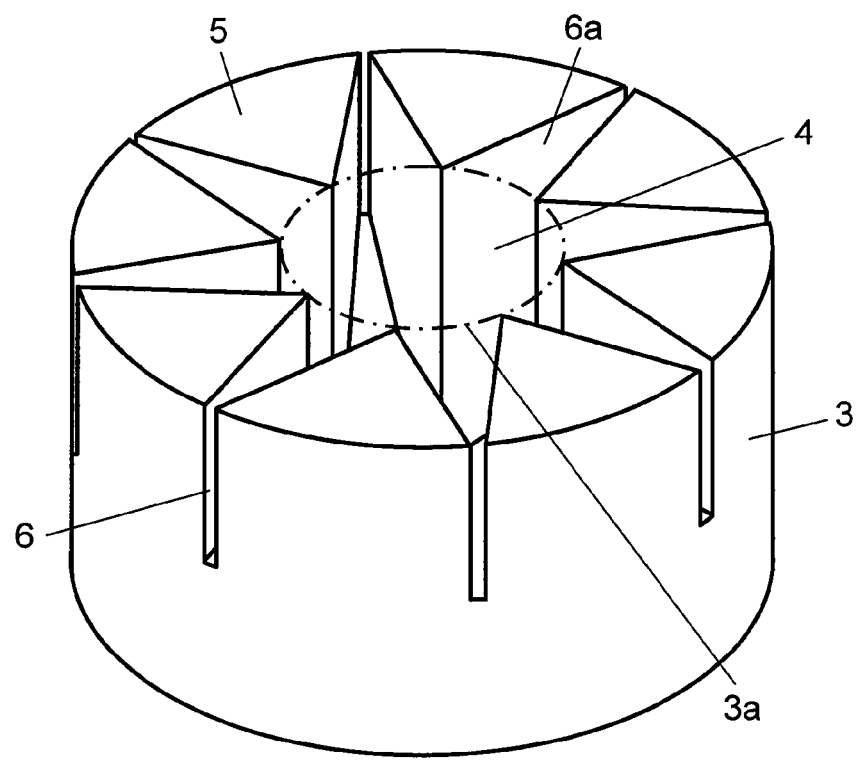
FIG. 6 is a perspective view of a cell electrophysiological sensor in accordance with a third exemplary embodiment of the present invention.
Figure 7:
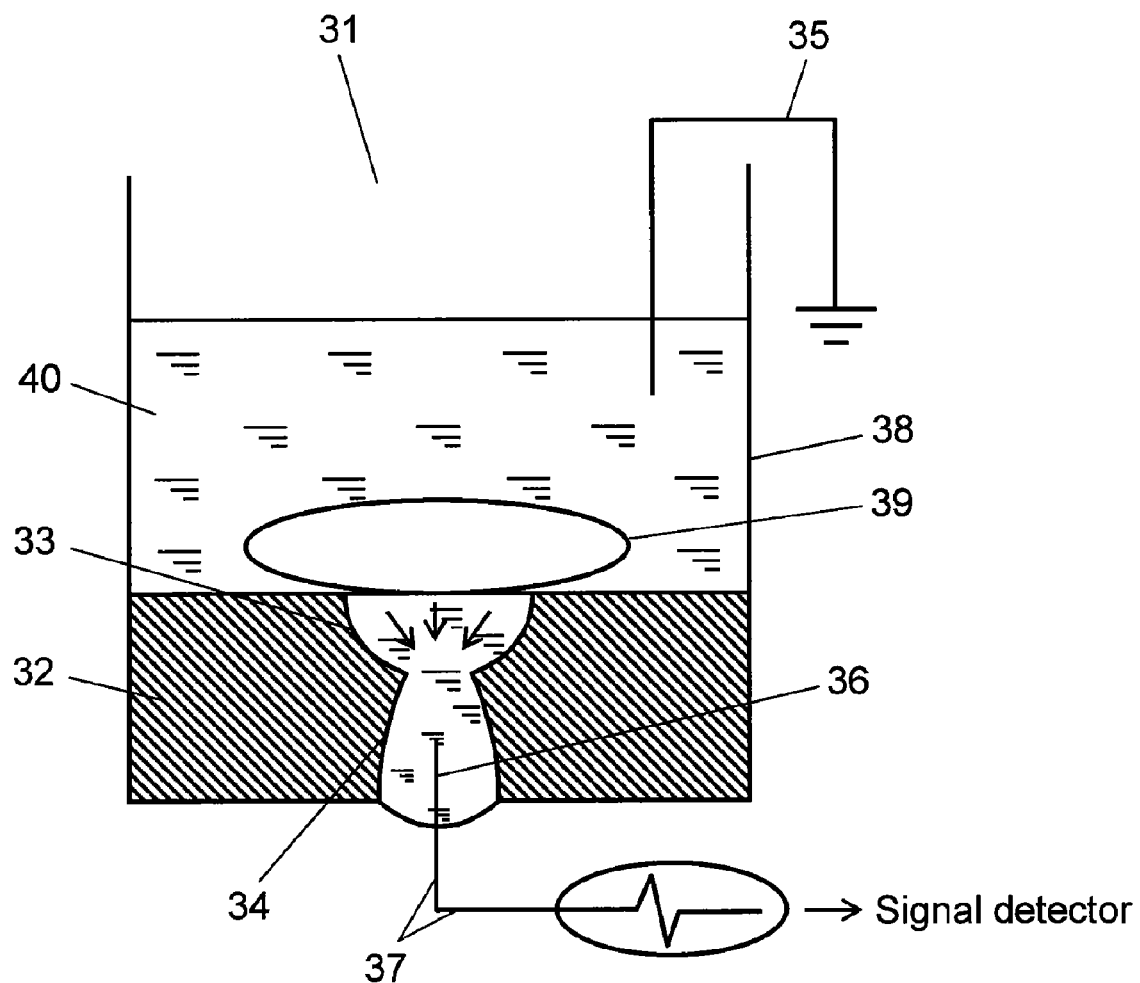
FIG. 7 is a sectional view of a conventional extracellular potential measuring sensor.

A description is provided for a cell electrophysiological sensor in accordance with the third exemplary embodiment of the present invention with reference to FIG. 6. FIG. 6 is a perspective view of the cell electrophysiological sensor in accordance with the third exemplary embodiment.

The structure of the cell electrophysiological sensor of this exemplary embodiment largely differs from that of the cell electrophysiological sensor of the first exemplary embodiment in the following point: kerfs 6 are formed in a radial configuration so that frame 3 has no inner wall surface in inner circumferential part 3a of frame 3. Such a configuration can be formed by adjusting the shapes of kerfs 6 or the number of kerfs 6. In this manner, a sensor structure that has no wall surface in inner circumferential part 3a of frame 3 can be formed by optimizing the opening shapes of kerfs 6.

With this structure, a cell electrophysiological sensor capable of suppressing the occurrence of bubbles and efficiently removing remaining bubbles can be provided. The cell electrophysiological sensor having such a structure can be produced easily in terms of productivity, by forming kerfs 6, using an etching or laser machining device.

Further, the advantage similar to that of the second exemplary embodiment can be provided by forming the bottom surfaces of kerfs 6 so that the bottom surfaces are inclined toward the center of diaphragm 2 as describe in the second exemplary embodiment.

In each of the above first through third exemplary embodiments, a cell electrophysiological sensor is described as an example of a biosensor. The present invention can be applied to various biosensors for measuring other specimens, such as a DNA, RNA, protein, amino acid, lipid membrane, carbohydrate, ion, antigen, or the like. In these cases, the specimen holder is a receptor, e.g. a DNA probe, an electrode, an antigen, or the like.

Industrial Applicability

The biosensor of the present invention is capable of suppressing the occurrence of bubbles and easily removing remaining bubbles. Thus the measuring reliability of the biosensor can be improved. For this reason, the present invention is useful as a biosensor in a medical field where high-accuracy measurement is required.

The invention claimed is:

1. A biosensor comprising:
a diaphragm having a specimen holder; and
a frame supporting the diaphragm and having a cavity,
wherein a kerf is formed in the frame so as to have a dimension extending from the diaphragm to an end surface of the frame, the end surface being external to the cavity, and wall surfaces of the kerf are made hydrophilic.

2. The biosensor of claim 1, wherein the kerf is one of a plurality of kerfs formed in a radial configuration.

3. The biosensor of claim 2, wherein at least two of the kerfs have different widths.

4. The biosensor of claim 2, wherein the kerfs are formed so as not to form a wall surface in an inner circumferential part of the frame.

5. The biosensor of claim 1, wherein a width of the kerf is increased from an outer circumferential part to an inner circumferential part of the frame.

6. The biosensor of claim 1, wherein a bottom surface of the kerf is flush with the diaphragm.

7. The biosensor of claim 1, wherein a bottom surface of the kerf is inclined with respect to the diaphragm.

8. A biosensor comprising:
a diaphragm having a specimen holder; and
a frame supporting the diaphragm and having a cavity,
wherein a plurality of kerfs are formed in the frame so as to extend from an end surface of the frame,
the plurality of kerfs are formed so as not to form a wall surface in an inner circumferential part of the frame,
and wall surfaces of the kerfs are made hydrophilic.

* * * * *